United States Patent

Stanetty et al.

[11] Patent Number: 5,814,629
[45] Date of Patent: Sep. 29, 1998

[54] MICROBICIDES

[75] Inventors: Peter Stanetty, Harmannsdorf, Austria; Walter Kunz, Oberwil, Switzerland

[73] Assignee: Novartis Finance Corporation, New York, N.Y.

[21] Appl. No.: 770,074

[22] Filed: Dec. 19, 1996

[30] Foreign Application Priority Data

Dec. 20, 1995 [CH] Switzerland .......................... 03613/95

[51] Int. Cl.⁶ .................... H01N 43/878; H01N 43/84; C07D 513/04
[52] U.S. Cl. .................... 514/234.2; 504/225; 504/249; 504/261; 514/322; 514/361; 544/134; 546/199; 548/126
[58] Field of Search ............... 548/126; 514/361, 514/322, 234.2; 546/199; 544/134; 504/25, 249, 261

[56] References Cited

U.S. PATENT DOCUMENTS

| 4,795,817 | 1/1989 | Chenard | 548/370 |
| 5,190,928 | 3/1993 | Schurter et al. | 514/63 |
| 5,260,423 | 11/1993 | Kunz et al. | 536/618 |
| 5,384,321 | 1/1995 | Kunz et al. | 504/261 |
| 5,616,590 | 4/1997 | Maetzke | 514/301 |

FOREIGN PATENT DOCUMENTS 9313664  7/1993  WIPO .

OTHER PUBLICATIONS

Hurd et al., J. Amer. Chem. Soc., 77, pp. 5359–5364 (1955).
Gewald et al., J. f. prakt Chemie., 330, No. 6, pp. 866–872 (1988).

Primary Examiner—Richard L. Raymond
Attorney, Agent, or Firm—Gabriel Lopez

[57] ABSTRACT

The invention relates to novel microbicidal and plant-immunising compounds of formula I

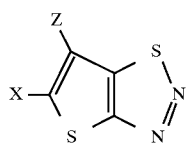

wherein:

X is hydrogen, halogen, $C_1$–$C_4$alkyl, $SR_8$, $N(R_9)R_{10}$, $CH_2OH$, CHO or $COOR_8$;

$R_8$ to $R_{10}$ are hydrogen, $C_1$–$C_4$alkyl, benzyl, $C_1$–$C_4$acyl or benzoyl;

Z is hydrogen, halogen, or a methyl group that is unsubstituted or to which from 1 to 3 unsubstituted or substituted hetero atoms O, S and/or N are bonded; in free form or in the form of salts. They can be used in crop protection for controlling and preventing disease infestation.

16 Claims, No Drawings

MICROBICIDES

The invention relates to novel microbicidal and plant-immunising compounds of formula I

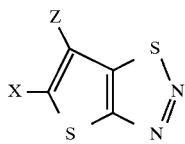

wherein:
X is hydrogen, halogen, $C_1$–$C_4$alkyl, $SR_8$, $N(R_9)R_{10}$, $CH_2OH$, CHO or $COOR_8$;
$R_8$ to $R_{10}$ are hydrogen, $C_1$–$C_4$alkyl, benzyl, $C_1$–$C_4$acyl or benzoyl;
Z is hydrogen, halogen, or a methyl group that is unsubstituted or to which from 1 to 3 unsubstituted or substituted hetero atoms O, S and/or N are bonded; in free form or in the form of salts.

The invention relates also to the preparation of those compounds, to agrochemical compositions comprising at least one of those compounds as active ingredient, and to the use of the compounds or of the compositions in the protection and immunisation of plants against attack by harmful microorganisms, for example fungi, bacteria and viruses.

The compounds of formula I and, where appropriate, their tautomers can be in the form of salts. Compounds of formula I that have at least one basic centre can form acid addition salts. The acid addition salts are formed, for example, with mineral acids, for example sulfuric acid, a phosphoric acid or a hydrohalic acid, with organic carboxylic acids, for example acetic acid, oxalic acid, malonic acid, maleic acid, fumaric acid or phthalic acid, hydroxycarboxylic acids, for example ascorbic acid, lactic acid, malic acid, tartaric acid or citric acid, or benzoic acid, or with organic sulfonic acids, for example methane- or p-toluene-sulfonic acid.

Furthermore, compounds of formula I having at least one acid group can form salts with bases. Suitable salts with bases are, for example, metal salts, such as alkali metal or alkaline earth metal salts, for example sodium, potassium or magnesium salts, or salts with ammonia or an organic amine, such as morpholine, piperidine, pyrrolidine, a mono-, di- or tri-lower alkylamine, for example ethyl-, diethyl-, triethyl- or dimethyl-propylamine, or a mono-, di- or tri-hydroxy-lower alkylamine, for example mono-, di- or tri-ethanolamine. Moreover, corresponding internal salts can also be formed, where appropriate. Within the scope of the invention, preference is given to agrochemically advantageous salts.

Unless defined otherwise, the general terms used hereinbefore and hereinafter have the meanings given below:

Hydrocarbon radicals may be saturated or unsaturated, open-chained or cyclic, or mixed open-chained and cyclic, for example cyclopropylmethyl or benzyl.

Depending upon the number of carbon atoms, alkyl groups are straight-chained or branched and are, for example, methyl, ethyl, n-propyl, isopropyl, n-butyl, sec-butyl, iso-butyl, tert-butyl, sec-amyl, tert-amyl, 1-hexyl or 3-hexyl.

Unsaturated hydrocarbon radicals are alkenyl, alkynyl or alkenynyl groups having not more than three multiple bonds, for example butadienyl, hexatrienyl or 2-penten-4-ynyl.

Alkenyl is to be understood as being straight-chained or branched alkenyl, for example allyl, methallyl, 1-methylvinyl or but-2-en-1-yl. Preference is given to alkenyl radicals having a chain length of 3 or 4 carbon atoms.

Alkynyl may likewise be straight-chained or branched, depending upon the number of carbon atoms, for example propargyl, but-1-yn-1-yl or but-1-yn-3-yl. Propargyl is preferred.

Cyclic unsaturated hydrocarbon radicals may be aromatic, for example phenyl and naphthyl, or non-aromatic, for example cyclopentenyl, cyclohexenyl, cycloheptenyl and cyclooctadienyl, or partially aromatic, for example tetrahydronaphthyl and indanyl.

Halogen, or halo, is fluorine, chlorine, bromine or iodine, preferably fluorine, chlorine or bromine.

Haloalkyl may contain identical or different halogen atoms, for example fluoromethyl, difluoromethyl, difluorochloromethyl, trifluoromethyl, chloromethyl, dichloromethyl, trichloromethyl, 2,2,2-trifluoroethyl, 2-fluoroethyl, 2-chloroethyl, 2,2,2-trichloroethyl, 3,3,3-trifluoropropyl.

Alkoxy is, for example, methoxy, ethoxy, propoxy, isopropoxy, n-butoxy, isobutoxy, sec-butoxy and tert-butoxy, preferably methoxy and ethoxy.

Haloalkoxy is, for example, difluoromethoxy, trifluoromethoxy, 2,2,2-trifluoroethoxy, 1,1,2,2-tetrafluoroethoxy, 2-fluoroethoxy, 2-chloroethoxy and 2,2-difluoroethoxy.

Cycloalkyl is cyclopropyl, cyclobutyl, cyclopentyl or cyclohexyl.

Alkanoyl is either straight-chained or branched. Examples are formyl, acetyl, propionyl, butyryl, pivaloyl and octanoyl.

A heterocyclyl radical is to be understood as being a 5- or 6-membered, aromatic or non-aromatic ring having hetero atoms N, O and/or S. Furthermore, an unsubstituted or substituted benzo group may be fused onto such a heterocyclyl radical bonded to the rest of the molecule. Examples of heterocyclyl groups are pyridyl, pyrimidinyl, imidazolyl, thiazolyl, 1,3,4-thiadiazolyl, triazolyl, thienyl, furanyl, pyrrolyl, morpholinyl, oxazolyl and the corresponding partially or completely hydrogenated rings. Examples of heterocyclyl groups to which a benzo group is fused are quinolyl, isoquinolyl, benzoxazolyl, quinoxalinyl, benzothiazolyl, benzimidazolyl, indolyl and indolinyl.

All the above-mentioned lists are given by way of example and do not represent any limitation.

Preferred groups are:
(1) Compounds of formula I wherein:
Z is hydrogen, CN, CO-A, CS-A or $CH(OR_1)_2$,
and wherein the other substituents are defined as follows:
A is hydrogen, halogen, $OR_2$, $SR_2$, $N(R_3)R_4$, NH—$OR_5$, O—N(=C)$_n$($R_6$)$R_7$ or
NH—N(=C)$_n$($R_6$)$R_7$;
the substituents $R_1$ are identical or different and are $C_1$–$C_4$alkyl that is unsubstituted or substituted by phenyl, $C_1$–$C_2$alkoxy, phenoxy or by benzyloxy; or
two substituents $OR_1$, together with the carbon atom to which they are bonded, form a cyclic acetal group that is unsubstituted or substituted by $C_1$–$C_3$alkyl, phenyl, benzyl, hydroxy or by $C_1$–$C_3$hydroxyalkyl;
$R_2$ to $R_7$ are hydrogen, an unsubstituted or substituted, open-chained, saturated or unsaturated hydrocarbon radical containing up to 8 carbon atoms, an unsubstituted or substituted, cyclic, saturated or unsaturated hydrocarbon radical containing up to 10 carbon atoms, unsubstituted or substituted benzyl or phenethyl, an unsubstituted or substituted acyl group containing up to 8 carbon atoms, an unsubstituted or substituted benzoyl group, or an unsubstituted or substituted heterocyclyl radical; or $R_3$ and $R_4$, together with the nitrogen atom to which they are bonded, form a 5- or 6-membered, unsubstituted or substituted carbocyclic or heterocyclic ring having from 1 to 3 hereto atoms O, S and/or N;

$R_6$ and $R_7$, together with the atom to which they are bonded, form a 5- to 7-membered, unsubstituted or substituted carbocyclic or heterocyclic ring having from 1 to 3 hetero atoms O, S and/or N; and n is 0 or 1; and wherein X is as defined for formula I.

(2) Compounds wherein:

the substituents $R_1$ are $C_1$–$C_4$alkyl, or two substituents $OR_1$, together with the carbon atom to which they are bonded, form a 5- to 7-membered cyclic acetal group that is unsubstituted or substituted by $C_1$–$C_3$alkyl;

$R_2$ and $R_3$ are hydrogen; $C_1$–$C_8$alkyl that is unsubstituted or substituted by from 1 to 5 halogen atoms, $C_3$–$C_6$cycloalkyl, $C_1$–$C_4$alkoxy, phenoxy, benzyloxy, $C_1$–$C_4$acyloxy, benzoyloxy, hydroxy, nitro, cyano, $C_1$–$C_4$alkanoyl, benzoyl, carboxy, $C_1$–$C_4$alkoxycarbonyl, benzyloxycarbonyl, amino, $C_1$–$C_4$alkylamino, $C_1$–$C_4$dialkylamino or by heterocyclyl; $C_3$–$C_6$-alkenyl that is unsubstituted or substituted by from 1 to 5 halogen atoms; $C_3$–$C_6$alkynyl; $C_3$–$C_6$cycloalkyl; $C_1$–$C_4$alkanoyl; phenyl, benzyl or phenethyl, the phenyl rings of which are unsubstituted or mono- to tri-substituted by halogen, hydroxy, $C_1$–$C_4$alkyl, halo-$C_1$–$C_2$alkyl, $C_1$–$C_2$alkoxy, halo-$C_1$–$C_2$alkoxy or by nitro; naphthyl, benzoyl or heterocyclyl, each of which is unsubstituted or mono- to tri-substituted by identical or different substituents selected from halogen, $C_1$–$C_2$alkyl, halomethyl and nitro;

$R_4$ is hydrogen, $C_1$–$C_6$alkyl or benzyl; or $R_3$ and $R_4$, together with the nitrogen atom to which they are bonded, form a 5- or 6-membered ring having 1 or 2 hetero atoms O, S and/or N, the said rings being unsubstituted or mono- or di-substituted by identical or different substituents selected from halogen, $C_1$–$C_3$alkyl and $C_1$–$C_2$alkoxycarbonyl;

$R_5$, $R_6$ and $R_7$ are each independently of the others hydrogen, $C_1$–$C_6$alkyl, $C_3$–$C_4$alkenyl, $C_3$–$C_4$alkynyl, $C_3$–$C_6$cycloalkyl, or phenyl or benzyl, the phenyl rings of which are unsubstituted or mono- or di-substituted by halogen, hydroxy, $C_1$–$C_2$alkyl, $C_1$–$C_2$alkoxy, halomethyl or by halomethoxy; or $R_6$ and $R_7$, together with the atom to which they are bonded, form a 5- to 7-membered carbocyclic or heterocyclic ring having from 1 to 3 hetero atoms O, S and/or N, the said rings being unsubstituted or mono- to tri-substituted by identical or different substituents selected from halogen and $C_1$–$C_3$alkyl; and wherein X is as defined for formula I.

(3) Compounds of formula I wherein:

Z is CO-A, CS-A or $CH(OR_1)_2$, and wherein

X is as defined for formula I.

(4) Compounds of formula I wherein:

Z is CO-A;

A is hydrogen, $OR_2$, $SR_2$, $N(R_3)R_4$, NH—$OR_5$, O—N(=C)$_n$($R_6$)$R_7$ or NH—N(=C)$_n$($R_6$)$R_7$; $R_2$ and $R_3$ are hydrogen; $C_1$–$C_8$alkyl that is unsubstituted or substituted by from 1 to 5 halogen atoms, $C_3$–$C_6$cycloalkyl, $C_1$–$C_4$alkoxy, phenoxy, benzyloxy, $C_1$–$C_4$acyloxy, benzoyloxy, hydroxy, nitro, cyano, $C_1$–$C_4$alkanoyl, benzoyl, carboxy, $C_1$–$C_4$alkoxycarbonyl, benzyloxycarbonyl, amino, $C_1$–$C_4$alkylamino, $C_1$–$C_4$dialkylamino or by heterocyclyl; $C_3$–$C_6$-alkenyl that is unsubstituted or substituted by from 1 to 5 halogen atoms; $C_3$–$C_6$alkynyl; $C_3$–$C_6$cycloalkyl; $C_1$–$C_4$alkanoyl; phenyl, benzyl or phenethyl, the phenyl rings of which are unsubstituted or mono- to tri-substituted by halogen, hydroxy, $C_1$–$C_4$alkyl, halo-$C_1$–$C_2$alkyl, $C_1$–$C_2$alkoxy, halo-$C_1$–$C_2$alkoxy or by nitro; naphthyl, benzoyl or heterocyclyl, each of which is unsubstituted or mono- to tri-substituted by identical or different substituents selected from halogen, $C_1$–$C_2$alkyl, halomethyl and nitro; or $R_3$ and $R_4$, together with the nitrogen atom to which they are bonded, form a 5- or 6-membered ring having 1 or 2 hetero atoms O, S and/or N, the said rings being unsubstituted or mono- or di-substituted by identical or different substituents selected from halogen and $C_1$–$C_3$alkyl;

$R_5$, $R_6$ and $R_7$ are each independently of the others hydrogen, $C_1$–$C_6$alkyl, $C_3$–$C_4$alkenyl, $C_3$–$C_4$alkynyl, $C_3$–$C_6$cycloalkyl, or phenyl or benzyl, the phenyl rings of which are unsubstituted or mono- or di-substituted by halogen, hydroxy, $C_1$–$C_2$alkyl, $C_1$–$C_2$alkoxy, halomethyl or by halomethoxy; or $R_6$ and $R_7$, together with the atom to which they are bonded, form a 5- to 7-membered carbocyclic or heterocyclic ring having from 1 to 3 hetero atoms O, S and/or N, the said rings being unsubstituted or mono- to tri-substituted by identical or different substituents selected from halogen, $C_1$–$C_3$alkyl and $C_1$–$C_2$alkoxycarbonyl; and wherein X is as defined for formula I.

(5) Compounds of formula I wherein:

Z is CO-A;

A is $OR_2$ or $SR_2$; of those compounds, especially those wherein:

$R_2$ is hydrogen; $C_1$–$C_6$alkyl that is unsubstituted or substituted by from 1 to 3 halogen atoms, $C_3$–$C_6$cycloalkyl, $C_1$–$C_2$alkoxy, phenoxy, hydroxy, cyano, $C_1$–$C_2$alkanoyl, benzoyl, carboxy, $C_1$–$C_4$alkoxycarbonyl, benzyloxycarbonyl, $C_1$–$C_2$acyloxy, benzoyloxy, amino, $C_1$–$C_4$alkylamino or by $C_1$–$C_4$dialkylamino; $C_3$–$C_4$alkenyl that is unsubstituted or substituted by from 1 to 3 halogen atoms; $C_3$–$C_4$alkynyl; $C_3$–$C_6$cycloalkyl; phenyl, benzyl or phenethyl, the phenyl rings of which are unsubstituted or mono- or di-substituted by halogen, hydroxy, $C_1$–$C_4$alkyl, halo-$C_1$–$C_2$alkyl, $C_1$–$C_2$alkoxy, halo-$C_1$–$C_2$alkoxy or by nitro.

(6) Compounds of formula I wherein:

Z is CO—$OR_2$.

(7) Compounds of formula I wherein:

Z is CN or CO—N($R_3$)$R_4$;

$R_3$ is hydrogen; $C_1$–$C_5$alkyl that is unsubstituted or substituted by from 1 to 3 halogen atoms, $C_3$–$C_6$cycloalkyl, $C_1$–$C_2$alkoxy, phenoxy, hydroxy, cyano, $C_1$–$C_2$alkanoyl, benzoyl, carboxy, $C_1$–$C_4$alkoxycarbonyl, benzyloxycarbonyl, $C_1$–$C_2$acyloxy, benzoyloxy, amino, $C_1$–$C_4$alkylamino or by $C_1$–$C_4$dialkylamino; $C_3$–$C_4$alkenyl that is unsubstituted or substituted by from 1 to 3 halogen atoms; $C_3$–$C_4$alkynyl; $C_3$–$C_6$cycloalkyl; phenyl, benzyl or phenethyl, the phenyl rings of which are unsubstituted or mono- or di-substituted by halogen, hydroxy, $C_1$–$C_4$alkyl, halo-$C_1$–$C_2$alkyl, $C_1$–$C_2$alkoxy, halo-$C_1$–$C_2$alkoxy or by nitro;

$R_4$ is hydrogen, $C_1$–$C_6$alkyl or benzyl; or $R_3$ and $R_4$, together with the nitrogen atom to which they are bonded, are pyrrolidine, piperidine, morpholine or dimethylmorpholine; and wherein X is as defined for formula I.

(8) Compounds of formula I wherein:

Z is CHO or $CH(OR_1)_2$;

the substituents $R_1$ are identical or different and are $C_1$–$C_4$alkyl that may be unsubstituted or substituted by phenyl, $C_1$–$C_2$alkoxy, phenoxy or by benzyloxy; or two substituents $OR_1$, together with the carbon atom to which they are bonded, form a 5- or 6-membered, cyclic acetal group that is unsubstituted or substituted by $C_1$–$C_3$alkyl, phenyl, benzyl, hydroxy or by $C_1$–$C_3$hydroxyalkyl; and wherein X is as defined for formula I.

(9) Compounds of formula I wherein:

Z is hydrogen, methyl, halogen, $C_1$–$C_4$alkoxymethyl or halomethyl.

(10) Compounds of formula I wherein:

X is hydrogen, halogen, methyl, mercapto, methylthio or amino; especially hydrogen.

Compounds of formula I can be prepared in accordance with Reaction scheme 1 as follows:

Reaction scheme 1

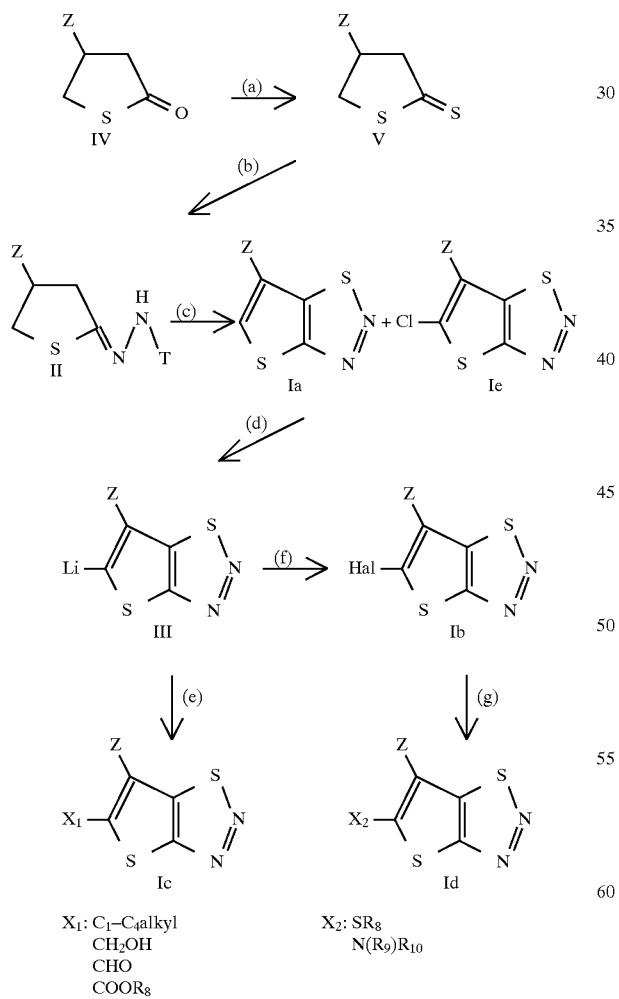

(a) If desired, thionation of a compound of formula IV with 4-methoxyphenylthiophosphonic acid cyclodithioanhydride ("Lawesson reagent") or phosphorus pentasulfide in an inert solvent, for example toluene or xylene, to form a dithiolactone of formula V.

(b) Reaction of a compound of formula V with a hydrazine derivative of the formula $H_2N$—NH—T, wherein T is a group CO—Y, $CONY_2$ or $SO_2$—Y and Y is hydrogen, unsubstituted or substituted $C_1$–$C_8$alkyl or unsubstituted or substituted aryl, or T is a group COO—U and U is unsubstituted or substituted $C_1$–$C_8$alkyl or unsubstituted or substituted aryl, in a polar solvent, for example an alcohol, such as ethanol or methanol, to form a compound of formula II.

(c) Cyclisation of a compound of formula II with thionyl chloride according to Hurd-Mori (C. D. Hurd, R. J. Mori, *J. Am. Chem. Soc.* 77, 5359 (1955)) to form a thieno-1,2,3-thiadiazole of formula Ia. In the cyclisation, the chlorinated compound Ie is also formed, depending upon the reaction conditions up to 25%.

(d) Reaction of a suitable compound Ia with an organolithium compound, for example butyllithium, sec-butyllithium, hexyllithium, lithium diisopropylamide (LDA), lithium hexamethyldisilazide or lithium tetramethylpiperidide (LTMP), in an aprotic solvent, for example THF, diethyl ether or hexane, in the presence or absence of an additional complexing agent at from –100° C. to +20° C. to form an organolithium compound of formula III.

(e) Reaction of III with a $C_1$–$C_4$alkyl halide or with formaldehyde or with dimethylformamide or with $CO_2$, and, where appropriate, subsequent esterification.

(f) Reaction of III with halogen or with hexachloroethane.

(g) Reaction of Ib with $HSR_8$ or $HN(R_9)R_4$ under basic conditions.

Compounds of formula IV wherein Z is hydrogen are known.

Compounds of formula IV wherein Z is as defined for formula I but is not hydrogen can be prepared in accordance with Reaction scheme 2 as follows:

Reaction scheme 2

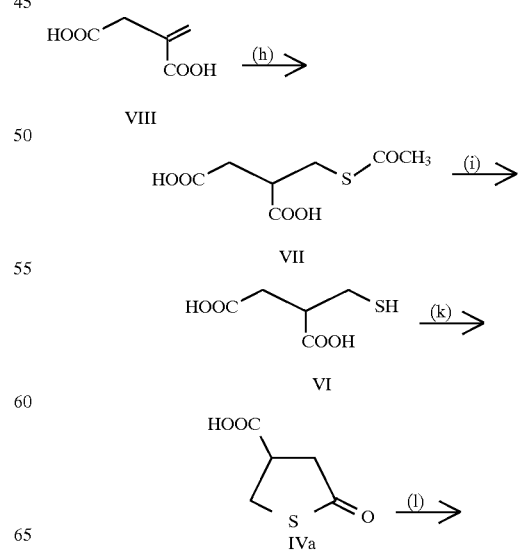

-continued
Reaction scheme 2

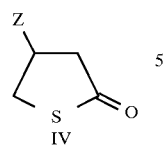

IV (h) Reaction of itaconic acid of formula VIII with thioacetic acid to form acetylthiomethyl-butanedioic acid of formula VII (P. R. Dennis et al. Biochemistry, 25,1605 (1986); Suppl. Vol. 3, E III, p. 933).

(i) Hydrolysis of acetylthiomethylbutanedioic acid of formula VII to mercaptomethylbutanedioic acid of formula VI (J. P. Danehy, Int. J. Sulfur Chem. Part C, 6,159 (1971); Suppl. Vol. 3, E III, p. 933, Vol. 3, E IV, p.1155).

(k) Cyclisation of mercaptomethylbutanedioic acid by heating at from 100° C. to 160° C., with the removal of water, to form tetrahydro-5-oxo-3-thiophenecarboxylic acid of formula V (US 90-583537; Suppl. Vol.18, E III/IV, p. 5265).

(l) Conversion of the carboxy group into a group Z, wherein Z is as defined for formula I according to known methods, analogously to Reaction scheme 8.

Furthermore, compounds of formulae I and If to Ik can be prepared in accordance with Reaction schemes 4 to 8 as follows:

(n) Halogenation with a halogen, with or without a catalyst (such as Fe(Hal)$_3$, Sn(Hal)$_2$) Synth. Comm. 11, 25 (1981); J. Het. Chem. 32, 791; J. Chem. Soc. (B) 1971, 79; halogenation with PhSeHal (Hal=Cl, Br) in the presence of Al(Hal)$_3$ (Phosphorous, Sulfur and Silicon 53, 29 (1990)), halogenation with sulfuryl halide or N-halosuccinimide (Houben-Weyl, Heteroarene I, Part 1, Vol. E 6a, p. 415 ff), halogenation in the presence of a buffer (J. Het. Chem. 11, 205 (1974)).

Reaction scheme 4

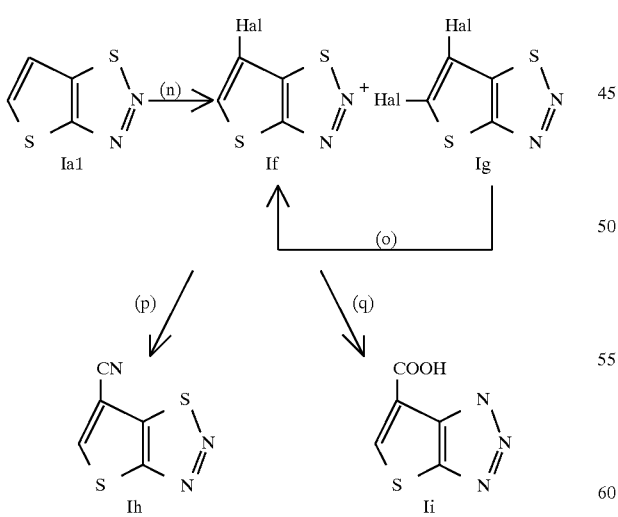

(o) Reduction, for example, with zinc/H$^+$(Bull. Chem. Soc. Jp. 66, 2033); with Na$_2$Te or Te/NaOH (Angew. Chem. 1967, 1106); by treatment with alkyllithium and subsequent protonation (Houben-Weyl, see above, p. 411 ff); dehalogenation by means of Cu/-quinoline.

(p) Reaction with CuCN in the presence of a complexing agent, such as pyridine, methylpyridine or quinoline, in an aprotic polar solvent (Rosenmund-vonBraun reaction).

(q) Reaction with carbon monoxide in the presence of a palladium catalyst (Heck reaction).

Reaction scheme 5

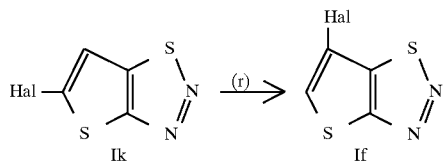

(r) Rearrangement by means of zeolite (Angew. Chem. 26, 470 (1987)); by means of alkali metal amide (Na/NH$_3$) Rec. trav. Chim. 93, 33 (1974)); Synth. Comm. 20, 1697 (1990)); J. Org. Chem 36, 2690 (1971)).

The reactions outlined in schemes 4 and 5 can be taken in part from Houben Weyl, Heteroarene I, Part 1, Vol. 6a, or from "Thiophene and its Derivatives", Heterocyclic Compounds, Edit. Weissberger/Taylor, New York 1992.

Reaction scheme 6

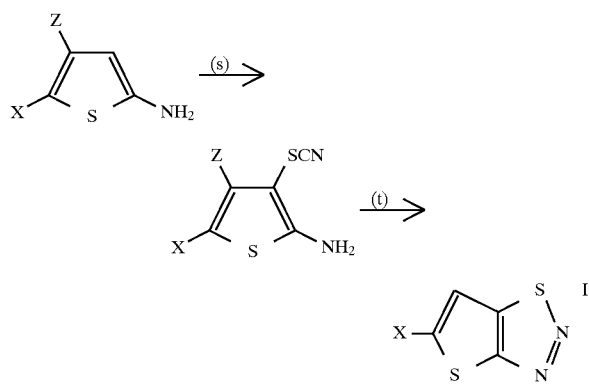

(s) Rhodanation with a rhodanide MSCN (M=an alkali metal atom or an NH$_4\oplus$ or heavy metal atom that may be polyvalent (e.g. Pb(SCN)$_2$) in the presence of an oxidising agent, such as H$_2$O$_2$, in an inert solvent at from −20° C. to 100° C. (preferably from −10° C. to +50° C.).

(t) Diazotisation or preliminary reduction of the −SCN group to −SH, for example by means of NaBH$_4$ in an inert solvent (e.g. alcohol, H$_2$O) at from −10° C. to 80° C. (preferably from 0° C. to 60° C.) and subsequent diazotisation with an alkali metal nitrite or alkyl nitrite in an inert solvent, where appropriate in the presence of a strong acid (H$_2$SO$_4$, HCl), at from −30° C. to +50° C. (preferably from −20° C. to +30° C.).

Reaction scheme 7

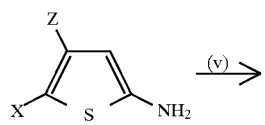

-continued
Reaction scheme 7

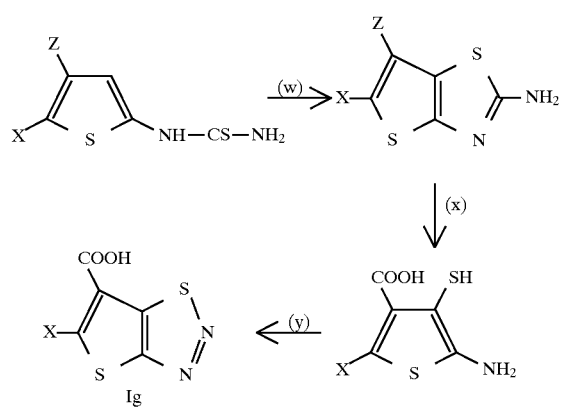

(v) SCN-/acid, for example $H_2SO_4$/inert solvent.
(w) Oxidising agent, for example $SO_2Cl_2$ or $Br_2$.
(x) Strong aqueous base, for example potassium hydroxide solution.

Reactions (v), (w) and (x) can be carried out, for example, analogously to Org. Synthesis Coll. Vol. III, p. 76; or J. Het. Chem. 17, 1325 (1980) or U.S. Pat. No. 5,374,737.

(y) Diazotisation with an alkali metal nitrite or alkyl nitrite in an inert solvent, where appropriate in the presence of a strong acid ($H_2SO_4$, HCl), at from $-30°$ C. to $+50°$ C. (preferably from $-20°$ C. to $+30°$ C.).

(ab) Reduction with iron in acetic acid.
(ac) Reaction with (t-BOC)$_2$O.
(ad) Diazotisation with an alkali metal nitrite or alkyl nitrite in a mixture of acetic acid and hydrochloric acid.

Compounds of formula I wherein Z is COOH can be converted by known methods into different compounds of the general formula I wherein Z is as defined for formula I. For example, the carboxylic acids can be converted with thionyl chloride into the corresponding carboxylic acid chlorides, from which the group Z can be converted in accordance with Reaction scheme 9 as follows:

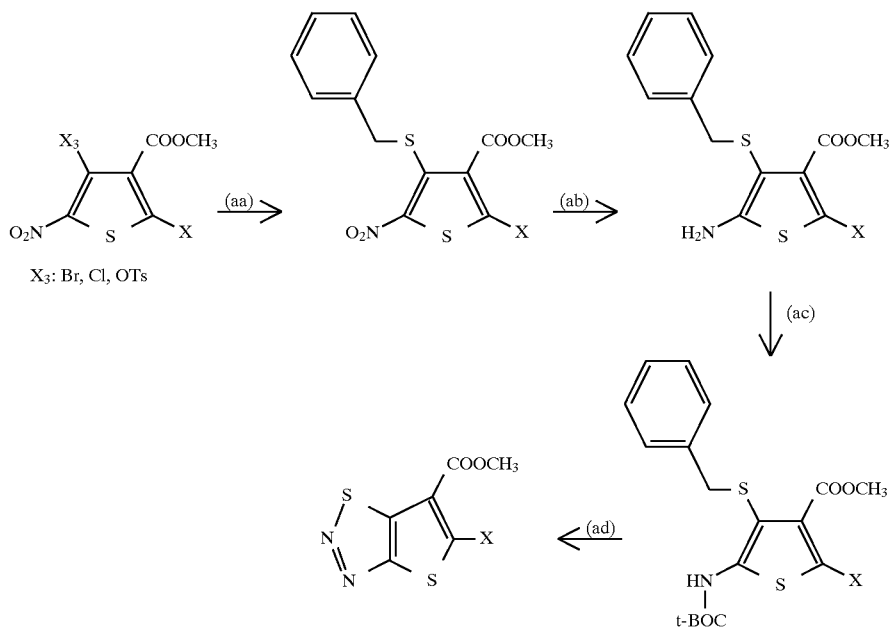

(aa) Replacement of a leaving group $X_3$ by benzylmercaptan in the presence of a base, for example $K_2O_3$, pyridine or triethylamine.

Reaction scheme 9

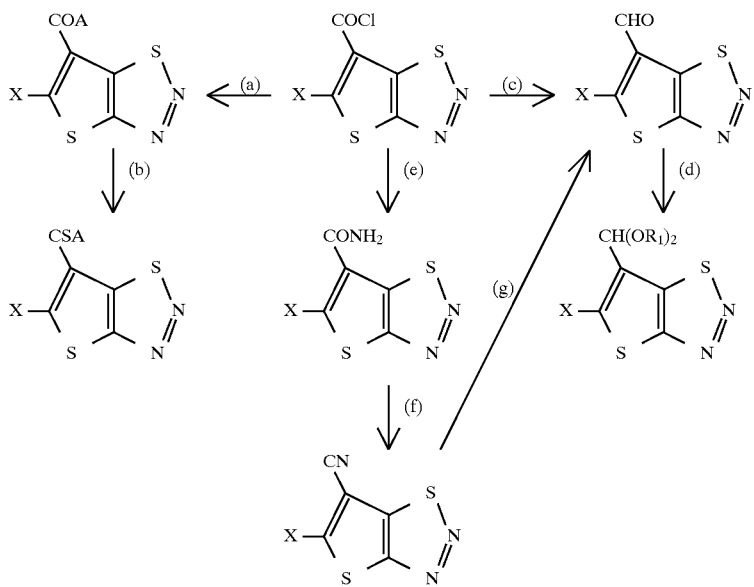

(a) Reaction with M—A, wherein M is hydrogen, Li$^+$, Na$^+$, K$^+$, ½ Mg$^{2+}$ or a quaternary ammonium ion and A is as defined for formula I.

(b) Reaction with a thionating agent, for example phosphorus pentasulfide or 4-methoxyphenylthiophosphonic acid cyclodithioanhydride ("Lawesson reagent").

(c) Reduction, for example, with hydrogen/catalyst or sodium borohydride.

(d) Acid-catalysed reaction with the corresponding alcohol or diol with the removal of water.

(e) Reaction with NH$_3$.

(f) Reaction with a water-removing agent, for example SOCl$_2$, POCl$_3$ or COCl$_2$.

(g) Reduction with diisobutylaluminium hydride.

Compounds of formula I wherein X=COOH can be converted by decarboxylation to X=H or by halodecarboxylation to X=halogen.

Suitable bases are, for example, alkali metal or alkaline earth metal hydroxides, hydrides, amides, alkanolates, carbonates, dialkylamides and alkylsilylamides, alkylamines, alkylenediamines, N-unsubstituted or N-alkylated, saturated or unsaturated cycloalkylamines, basic heterocycles, ammonium hydroxides and carbocyclic amines. There may be mentioned by way of example sodium hydroxide, hydride, amide, methanolate and carbonate, potassium tert-butanolate and carbonate, lithium diisopropylamide, potassium bis(trimethylsilyl)amide, calcium hydride, triethylamine, triethylenediamine, cyclohexylamine, N-cyclohexyl-N,N-dimethylamine, N,N-diethylaniline, pyridine, 4-(N,N-dimethylamino)pyridine, N-methylmorpholine, benzyl-trimethyl-ammonium hydroxide and 1,8-diazabicyclo[5.4.0]undec-5-ene (DBU).

Examples of leaving groups are chlorine, bromine, iodine, $C_1$–$C_8$alkylthio, such as methylthio, ethylthio and propylthio, $C_1$–$C_8$alkanoyloxy, such as acetoxy, (halo-)$C_1$–$C_8$alkanesulfonyloxy, such as methanesulfonyloxy, ethanesulfonyloxy and trifluoromethanesulfonyloxy, or unsubstituted or substituted phenylsulfonyloxy, such as benzenesulfonyloxy and p-toluenesulfonyloxy, imidazolyl, hydroxy or water, preferably chlorine, bromine, iodine, trifluoromethanesulfonyloxy and p-toluenesulfonyloxy.

The reactants can be reacted with one another as such, that is to say without the addition of a solvent or diluent, for example in the molten state. In most cases, however, the addition of an inert solvent or diluent or of a mixture thereof is advantageous. There may be mentioned as examples of such solvents and diluents: aromatic, aliphatic and alicyclic hydrocarbons and halogenated hydrocarbons, such as benzene, toluene, xylene, chlorobenzene, bromobenzene, petroleum ether, hexane, cyclohexane, dichloromethane, trichloromethane, dichloroethane or trichloroethane; ethers, such as diethyl ether, tert-butyl methyl ether, tetrahydrofuran or dioxane; ketones, such as acetone or methyl ethyl ketone; alcohols, such as methanol, ethanol, propanol, butanol, ethylene glycol or glycerol; esters, such as ethyl acetate or butyl acetate; amides, such as N,N-dimethylformamide, N,N-dimethylacetamide, N-methylpyrrolidone or hexamethylphosphoric acid triamide; nitriles, such as acetonitrile; and sulfoxides, such as dimethyl sulfoxide. Bases used in excess, such as triethylamine, pyridine, N-methylmorpholine or N,N-diethylaniline, can also be used as solvents or diluents.

The reaction can also be carried out with phase-transfer catalysis in an organic solvent, for example methylene chloride or toluene, in the presence of an aqueous basic solution, for example sodium hydroxide solution, and of a phase-transfer catalyst, for example tetrabutylammonium hydrogen sulfate.

Typical reaction conditions will be seen from the Examples.

Where the compounds of formula I may be in the form of different stereoisomers, the invention relates both to the pure isomers and to all possible mixtures of isomers.

The invention relates also to novel starting materials and intermediates used in the preparation of the compounds of formula I, to the use thereof, and to processes for the preparation thereof.

In that respect, the following are of particular importance:

(1) the process for the preparation of a compound of formula Ia

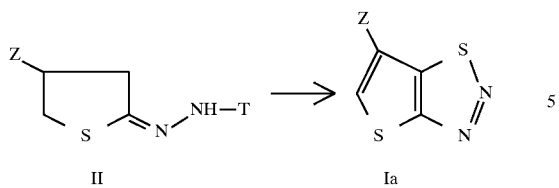

II → Ia wherein Z is as defined for formula 1, which comprises reacting with thionyl chloride a compound of formula II wherein T is a group CO—Y, CONY$_2$ or SO$_2$—Y and Y is hydrogen, unsubstituted or substituted C$_1$–C$_8$alkyl or unsubstituted or substituted aryl, or T is a group COO—U and U is unsubstituted or substituted C$_1$–C$_8$alkyl or unsubstituted or substituted aryl;

(2) the process for the preparation of a compound of formula I

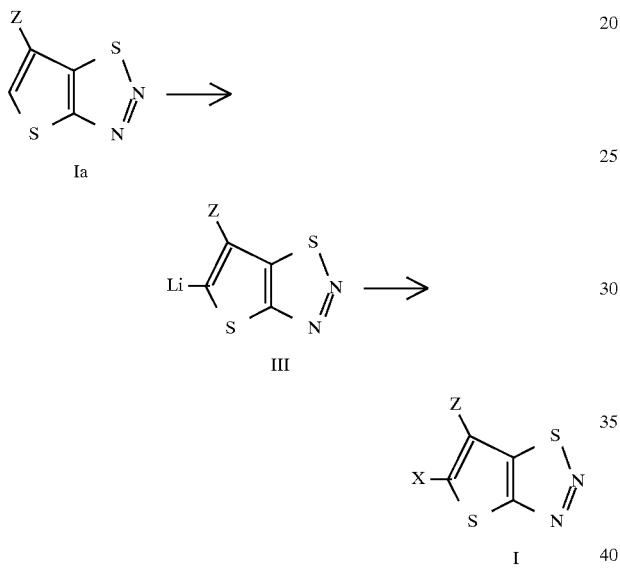

Ia → III → I wherein X and Z are as defined for formula I, which comprises reacting a compound of formula Ia wherein Z is as defined for formula I with an organolithium compound, for example butyllithium, sec-butyllithium, hexyllithium, lithium diisopropylamide (LDA), lithium hexamethyldisilazide or lithium tetramethylpiperidide (LTMP), in an aprotic solvent, for example THF, diethyl ether or hexane, in the presence or absence of an additional complexing agent, at from −100° C. to +20° C., to form an organolithium compound of formula III, and reacting that compound further
a) for the preparation of a compound wherein X is halogen, with a halogen;
b) for the preparation of a compound wherein X is chlorine, with hexachloroethane;
c) for the preparation of a compound wherein X is C$_1$–C$_4$alkyl, with a C$_1$–C$_4$alkyl halide;
d) for the preparation of a compound wherein X is CH$_2$OH, with formaldehyde;
e) for the preparation of a compound wherein X is CHO, with dimethylformamide;
f) for the preparation of a compound wherein X is COOR$_8$, with CO$_2$ and then, where appropriate, esterifying the compound thus obtained;

(3) the process for the preparation of an organolithium compound of formula III

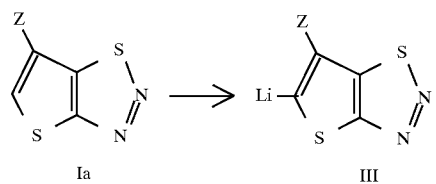

Ia → III wherein Z is as defined for formula I, which comprises reacting a compound of formula Ia wherein Z is as defined for formula I with an organolithium compound, for example butyllithium, sec-butyllithium, hexyllithium, lithium diisopropylamide (LDA), lithium hexamethyldisilazide or lithium tetramethylpiperidide (LTMP), in an aprotic solvent, for example THF, diethyl ether or hexane, in the presence or absence of an additional complexing agent, at from −100° C. to +20° C., to form an organolithium compound of formula III; and (4) the process for the preparation of a compound of formula I

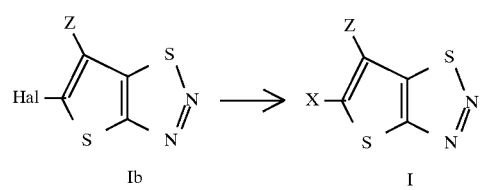

Ib → I wherein Z is as defined for formula I and X is SR$_8$ or N(R$_9$)R$_{10}$, which comprises reacting a compound of formula Ib wherein Hal is halogen with HSR$_8$ or HN(R$_9$)R$_{10}$ under basic conditions.

Preferred intermediates are the compounds of formula II

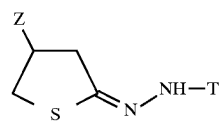

II wherein Z is as defined for formula I and T is a group CO—Y, CONY$_2$ or SO$_2$—Y and Y is hydrogen, unsubstituted or substituted C$_1$–C$_8$alkyl or unsubstituted or substituted aryl, or T is a group COO—U and U is unsubstituted or substituted C$_1$–C$_8$alkyl or unsubstituted or substituted aryl, but is especially COO—C$_1$–C$_4$alkyl;

also organolithium compounds of formula III

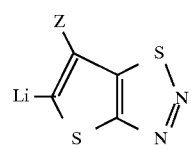

III wherein Z is as defined for formula I, in the form of a solution in an aprotic solvent.

Thieno-1,2,3-thiadiazoles are described generically in EP-A-138 622; that reference does not, however, provide any examples or indicate any methods of preparation. Furthermore, 6-methyl-5-ethoxycarbonyl-thieno[2,3-d]-1,2,3-thiadiazole X

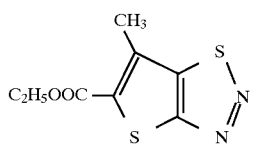

is described in J. prakt. Chem. 330, p. 866–872 (1988) without mention of any application; that compound differs from the compounds of the present invention in the nature of the substituents.

Compounds of formula I are novel and have an unexpectedly high degree of microbial activity. Plants can be protected both by direct action on the pests and by activation and stimulation of the plant's own defence system (immunisation). That mode of action has also become known by the name "Systemic Activated Disease Resistance" ("SAR"). Accordingly, using the compounds of the invention, plants can be kept healthy and strengthened by their own resources.

The compounds of formula I can be used in the agricultural sector and related fields preventively and/or curatively as active ingredients in the control of plant pests. The compounds of formula I according to the invention are distinguished by excellent action even at low rates of concentration and by the fact that they are well tolerated by plants and are environmentally friendly. They have very advantageous, especially systemic, properties and can be used to protect numerous cultivated plants. The compounds of formula I can be used to inhibit or destroy the pests which occur on plants or on parts of plants (the fruit, blossom, leaves, stems, tubers or roots) of different crops of useful plants, while at the same time parts of plants that grow later are also protected, for example against phytopathogenic microorganisms.

The compounds I can also be used as dressings in the treatment of seed (fruit, tubers, grains) and plant cuttings to provide protection against fungus infections as well as against phytopathogenic fungi which occur in the soil.

The compounds I are effective, for example, against phytopathogenic fungi belonging to the following classes: Fungi imperfecti (e.g. Botrytis, Pyricularia, Helminthosporium, Fusarium, Septoria, Cercospora and Alternaria) and Basidiomycetes (e.g. Rhizoctonia, Hemileia, Puccinia). Moreover, they are effective against the classes of the Ascomycetes (e.g. Venturia and Erysiphe, Podosphaera, Monilinia, Uncinula) and Oomycetes (e.g. Phytophthora, Pythium, Plasmopara).

Target crops to be protected within the scope of the present invention comprise e.g. the following species of plants: cereals (wheat, barley, rye, oats, rice, maize, sorghum and related species); beet (sugar beet and fodder beet); pomes, stone fruit and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (marrows, cucumber, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocados, cinnamon, camphor); and plants such as tobacco, nuts, coffee, aubergines, sugar cane, tea, pepper, vines, hops, bananas and natural rubber plants, as well as ornamentals.

The compounds I are generally used in the form of compositions and can be applied to the crop area or plant to be treated, simultaneously or in succession, with further compounds. These further compounds can be, for example, fertilisers or micronutrient donors or other preparations that influence plant growth. They can also be selective herbicides as well as insecticides, fungicides, bactericides, nematicides, molluscicides or mixtures of several of these preparations, if desired together with further carriers, surfactants or other application-promoting adjuvants customarily employed in formulation technology.

Suitable carriers and adjuvants can be solid or liquid and are the substances ordinarily employed in formulation technology, e.g. natural or regenerated mineral substances, solvents, dispersants, wetting agents, tackifiers, thickeners, binders or fertilisers.

A preferred method of applying a compound of formula I, or an agrochemical composition comprising at least one of those compounds, is application to the leaves (foliar application). The frequency and rate of application depend upon the risk of infestation by the corresponding pathogen. The compounds I can, however, also penetrate the plant through the roots via the soil (systemic action) if the locus of the plant is impregnated with a liquid formulation or if the substances are introduced in solid form into the soil, e.g. in the form of granules (soil application). In paddy rice crops, such granules can be applied in metered amounts to the flooded rice field. In order to treat seed, the compounds I can, however, also be applied to the seeds (coating), either by impregnating the grains or tubers with a liquid formulation of the active ingredient, or by coating them with a solid formulation.

The compounds I are used in unmodified form or, preferably, together with the adjuvants conventionally employed in formulation technology. For that purpose they are advantageously formulated in known manner e.g. into emulsifiable concentrates, coatable pastes, directly sprayable or dilutable solutions, dilute emulsions, wettable powders, soluble powders, dusts or granules, for example by encapsulation in e.g. polymer substances. As with the nature of the compositions, the methods of application, such as spraying, atomising, dusting, scattering, coating or pouring, are chosen in accordance with the intended objectives and the prevailing circumstances.

Advantageous rates of application are normally from 5 g to 2 kg of active ingredient (a.i.) per hectare (ha), preferably from 10 g to 1 kg a.i./ha, especially from 20 g to 600 g a.i./ha. When the compounds are used as seed dressings, dosages of from 10 mg to 1 g of active ingredient per kg of seed are advantageously employed.

The formulations, i.e. the compositions, preparations or mixtures comprising the compound (active ingredient) of formula I and, where appropriate, a solid or liquid adjuvant, are prepared in known manner, e.g. by homogeneously mixing and/or grinding the active ingredient with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates, such as dibutyl phthalate or dioctyl phthalate, aliphatic hydrocarbons, such as cyclohexane or paraffins, alcohols and glycols and their ethers and esters, such as ethanol, ethylene glycol, ethylene glycol monomethyl or monoethyl ether, ketones, such as cyclohexanone, strongly polar solvents, such as N-methyl-2-pyrrolidone, dimethyl sulfoxide or dimethylformamide, as well as vegetable oils or epoxidised vegetable oils, such as epoxidised coconut oil or soybean oil; and water.

The solid carriers used, e.g. for dusts and dispersible powders, are normally natural mineral fillers, such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite, and suitable nonsorbent carriers are, for example, calcite or sand. In addition, a great number of pregranulated materials of inorganic or organic nature can be used, e.g. dolomite or pulverised plant residues.

Depending upon the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and water-soluble synthetic surface-active compounds are suitable anionic surfactants.

Representative examples of non-ionic surfactants are nonylphenolpolyethoxyethanols, castor oil polyglycol ethers, polypropylene/polyethylene oxide adducts, tributylphenoxypolyethleneethanol, polyethylene glycol and octylphenoxypolyethoxyethanol. Also suitable are fatty acid esters of polyoxyethylene sorbitan, e.g. polyoxyethylene sorbitan trioleate.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals.

Further surfactants customarily employed in formulation technology are known to the person skilled in the art or can be taken from the relevant specialist literature.

The agrochemical compositions generally comprise 0.1 to 99% by weight, preferably 0.1 to 95% by weight, of a compound of formula I 99.9 to 1% by weight, preferably 99.8 to 5% by weight, of a solid or liquid adjuvant and 0 to 25% by weight, preferably 0.1 to 25% by weight, of a surfactant.

Whereas commercial products will preferably be formulated as concentrates, the end user will normally employ dilute formulations.

The compositions may also comprise further auxiliaries, such as stabilisers, antifoams, viscosity regulators, binders or tackifiers, as well as fertilisers or other active ingredients for obtaining special effects.

EXAMPLES

1. Preparation Examples

Example 1

Preparation of acetylthiomethylbutanedioic acid (VII) (intermediate)

400 g (3.07 mol) of itaconic acid (VIII) are added in portions within a period of approximately 30 minutes to 280 g (3.68 mol) of thioacetic acid, with simultaneous heating of the heating bath to 95° C. After 2.5 hours' stirring at 90°–100° C., the reaction mixture is cooled to room temperature and diluted with 300 ml of diisopropyl ether (DIPE), whereupon the product crystallises out within a period of approximately 12 hours. There are obtained 582 g of crystals having a melting point of 89°–91° C.

Example 2

Preparation of mercaptomethylbutanedioic acid (VI) (intermediate)

582 g (2.85 mol) of acetylthiomethylbutanedioic acid (VII) are added, under nitrogen and while cooling with ice, to a solution of 570 g (14.25 mol) of NaOH in 3 litres of water (exothermic reaction). After 15 hours' stirring at room temperature, the reaction mixture is acidified to pH 1 with concentrated hydrochloric acid and extraction is carried out with ether. The combined organic phases are dried over sodium sulfate and concentrated to dryness, and the crystalline residue is washed with 200 ml of cold dichloromethane. There are obtained 385 g of crystals having a melting point of 107°–108.5° C.

Example 3

Preparation of tetrahydro-5-oxo-3-thiophenecarboxylic acid (IVa) (intermediate)

A molten mass of 385 g (2.34 mol) of mercaptomethylbutanedioic acid (VI) is heated at 140°–150° C. for 3 hours. After cooling to room temperature there are obtained 315 g of solidified product having a melting point of 106°–108° C.

Example 4

Preparation of tetrahydro-5-oxo-3-thiophenecarboxylic acid methyl ester (intermediate)

225 g (1.09 mol) of dicyclohexylcarbodiimide (DCC) are added in portions, while cooling with ice, to a solution of 160 g (1.095 mol) of tetrahydro-5-oxo-3-thiophenecarboxylic acid, 70 g (2.19 mol) of methanol and 4 g (32.8 mmol) of dimethylaminopyridine (DMAP) in 2.5 litres of diethyl ether. After 4 hours' stirring at room temperature, the dicyclohexylurea is filtered off and the filtrate is extracted with 500 ml of 2N hydrochloric acid and 500 ml of saturated sodium hydrogen carbonate solution, is washed with water and is dried over sodium sulfate. There are obtained 149 g of solid product having a melting point of 33°–35° C.

Example 5

Preparation of tetrahydro-5-thioxo-3-thiophenecarboxylic acid methyl ester (intermediate)

207 g (0.51 mol) of Lawesson reagent are added at room temperature to a suspension of 149 g (0.93 mol) of tetrahydro-5-oxo-3-thiophenecarboxylic acid methyl ester in 1.23 litres of absolute toluene, and the mixture is boiled at reflux for 16 hours. Then the solvent is removed by distillation in vacuo, the residue is boiled at reflux for 20 minutes four times in one litre of a solvent mixture of petroleum ether and diethyl ether 1:1 each time, and the extract phase is in each case decanted off and concentrated. After distillation of the crude substance at 130°–140° C./0.03 mbar using a bulb tube, 129.5 g of orange oil are obtained.

Example 6

Preparation of 5-(2-ethoxycarbonyl-2-hydrazinyl-1-ylidene)-tetrahydro-3-thiophenecarboxylic acid methyl ester (IIa) (intermediate)

149 g (1.43 mol) of hydrazinecarboxylic acid ethyl ester are added in portions at room temperature to a solution of 253 g (1.43 mol) of tetrahydro-5-thioxo-3-thiophenecarboxylic acid methyl ester in absolute ethanol, and the mixture is boiled at reflux for 4 hours. The reaction mixture is concentrated to dryness and the residue is recrystallised from 200 ml of isopropanol. There are obtained 315.6 g of crystalline product having a melting point of 89°–91° C.

Example 7

Preparation of thieno[2,3-d]1,2,3-thiadiazole-6-carboxylic acid methyl ester

To a solution of 315.6 g (1.28 mol) of 5-(2-ethoxycarbonyl-2-hydrazinyl-1-ylidene)-tetrahydro-3-thiophenecarboxylic acid methyl ester in 2 litres of dichloromethane there are slowly added dropwise, while cooling with ice, 3044 g (25.6 mol) of thionyl chloride in such a manner that the solvent does not begin to boil. Then the reaction mixture is stirred at room temperature for 16 hours, the solvent and excess thionyl chloride are removed by distillation, the residue is digested with 2 litres of ethyl acetate for 30 minutes, and the solid obtained after removal of the solvent is recrystallised. There are obtained 155.3 g of crystalline product having a melting point of 139°–141° C. that still contains approximately 4% 5-chlorothieno[2,3-d]1,2,3-thiadiazole-6-carboxylic acid methyl ester as secondary product.

Example 8
Preparation of thieno[2,3-d]2,3-thiadiazole-6-carboxylic acid

A solution of 58 g (1.45 mol) of NaOH in 400 ml of water is added to a suspension of 145 g (0.724 mol) of thieno[2,3-d]1,2,3-thiadiazole-6-carboxylic acid methyl ester (Ia) in ethanol, and the mixture is stirred at room temperature for 90 minutes. Then the ethanol is largely removed by distillation, the solution that remains is acidified, while cooling with ice, with 130 ml of concentrated hydrochloric acid, and the product is isolated by filtration, washed with water and dried. There are obtained 131.5 g of crystalline product having a melting point of 268°–272° C. (decomposition).

Example 9
Preparation of 5-chlorothieno[2,3-d]1,2,3-thiadiazole-6-carboxylic acid 79 ml (201.6 mmol) of n-butyllithium (1.6M in hexane) are added at –30° C., under nitrogen, to a solution of 20.4 g (201.6 mmol) of diusopropylamine in 200 ml of tetrahydrofuran (THF). After 20 minutes' stirring at –20° C., the LDA solution so prepared is added dropwise at –90° C., under nitrogen, by means of a capillary, to a suspension of 15.0 g (80.6 mmol) of thieno[2,3-d]1,2,3-thiadiazole-6-carboxylic acid in 150 ml of THF. After 90 minutes' stirring at –50° C., a solution of 42.0 g (177.2 mmol) of hexachloroethane in 70 ml of THF is added at –90° C. and the reaction mixture is heated to room temperature within a period of 2 hours. Then the reaction mixture is poured onto 2 litres of water, the aqueous phase is extracted with diethyl ether and acidified with concentrated hydrochloric acid, and the product is isolated by filtration. There are obtained 17.55 g of light-brown solid having a melting point of 255°–265° C. (decomposition).

Example 10
Preparation of 5-chlorothieno[2,3-d]1,2,3-thiadiazole-6-carboxylic acid methyl ester 50.70 g (246 mmol) of dicyclohexylcarbodiimide (DCC) are added in small portions, at room temperature and with vigorous stirring, to a solution of 54.28 g (246 mmol) of 5-chlorothieno[2,3-d]1,2,3-thiadiazole-6-carboxylic acid, 39.40 g (1.23 mol) of methanol and 2.00 g (16.4 mmol) of 4-dimethylaminopyridine (DMAP) in one litre of dichloromethane. After 16 hours' stirring, the dicyclohexylurea is isolated by filtration and washed with dichloromethane. The combined organic phases are extracted once with each of 2N hydrochloric acid, saturated sodium hydrogen carbonate solution and water, are dried over sodium sulfate and are concentrated to dryness. The residue is chromatographed on 500 g of silica gel 60 with dichloromethane/petroleum ether 1:1. There are obtained 45.3 g of a colourless solid having a melting point of 124°–126° C.

Example 11
Preparation of thieno[2,3-d]1,2,3-thiadiazole and 5-chlorothieno[2,3-d]1,2,3-thiadiazole of formulae Ia1 and Ik, respectively 20 ml of thionyl chloride dissolved in 20 ml of dichloromethane are added dropwise at room temperature, under a nitrogen atmosphere and with stirring, to a solution of 9.5 g of 5-(2-ethoxycarbonyl-2-hydrazinyl-1-ylidene)-tetrahydrothiophene in 100 ml of dichloromethane, the internal temperature rising to approximately 35° C. after a short time and the evolution of gaseous hydrogen chloride beginning. The mixture is stirred at room temperature overnight and then for a further 3 hours under reflux, concentration by evaporation is carried out, and the residue is partitioned between ethyl acetate and ice-water. The organic extracts are washed with water, dried and concentrated by evaporation. The residue is purified on silica gel (hexane/ethyl acetate 9:1) to yield in succession 5-chlorothieno[2,3-d]1,2,3-thiadiazole Ia1 having a melting point of 117°–119° C. and, as the main product, thieno[2,3-d]1,2,3-thiadiazole Ia2 having a melting point of 78°–79° C.

The reaction can also be carried out in other solvents, for example toluene. In addition, the reactants can be reacted in reverse order, for example by adding a solution of the carbazone in toluene dropwise at 70° C. to a solution, heated to that temperature, of the thionyl chloride in toluene and stirring until the reaction is complete.

Example 12
Preparation of 5-(2-ethoxycarbonyl-2-hydrazinyl-1-ylidine)-tetrahydrothiophene (intermediate)

A solution of 20.5 g of ethyl carbazate dissolved in 170 ml of warm ethanol is added to a solution of 23 g of tetrahydro-2-thioxothiophene and is boiled under reflux until the reaction is complete, hydrogen sulfide being released. The mixture is then concentrated by evaporation and the residue is made to crystallise by the addition of ethyl acetate and hexane. The precipitate is isolated by filtration, washed with hexane and dried, yielding the title compound having a melting point of 55°–57° C.

Example 13
Preparation of 2-amino-4-methoxymethylthiophene-5-carboxylic acid methyl ester hydrochloride (intermediate)

217 ml of diethylamine are added dropwise at a maximum of 25° C., with stirring and while cooling, to a mixture of 355 g of 3-methoxymethyl-5-cyano-pent-3-ene-carboxylic acid methyl ester (prepared analogously to J. prakt. Chem. 315, 542 (1973)), and 67.2 g of sulfur in one litre of ethanol, and stirring is carried out overnight at room temperature. The mixture is then cooled, and 1575 ml of concentrated hydrochloric acid are added dropwise at a maximum of 22° C. Further stirring at –5° C. yields a precipitate, which is isolated by filtration, washed with ether and recrystallised from dioxane. Colourless crystals having a melting point of 157°–158° C. are obtained.

Example 14
Preparation of 6-methoxymethyl-thieno[2.3-d]1,2,3-thiadiazole-5-carboxylic acid methyl ester In a sulfonating flask, 11 ml of concentrated sulfuric acid (96%) are added to 20 ml of ice-water, with stirring and while cooling, and 5.16 g of 2-amino-3-thiocyanato-4-methoxymethyl-5carboxylic acid methyl ester (prepared analogously to J. prakt. Chem. 315, 542 (1973)) are introduced in portions at –5° C. The suspension is diluted with 10 ml of dioxane and then, at from –3° C. to 0° C., a solution of 1.656 g of sodium nitrite in 2.8 ml of water is metered in beneath the surface and stirring is continued for ¾ hour at 0° C. Extraction is then carried out with dichloromethane, and the extracts are washed with water and dried, filtered and concentrated by evaporation. The oil that remains is purified on silica gel, yielding the title compound having a melting point of 123°–124° C.

Example 15
Preparation of thiomethoxycarbonyl-2-thienyl-thiourea (intermediate)

A solution of 3.9 g of 2-amino-4-thiophenecarboxylic acid methyl ester in 25 ml of chlorobenzene is cooled to −5° C., and 0.7 ml of concentrated sulfuric acid (96%) and 2.25 g of sodium rhodanide are added carefully at that temperature and stirring is carried out for 15 minutes at 0° C. and then for 5 hours at 100° C. The mixture is then cooled, taken up in warm tetrahydrofuran, filtered over silica gel and concentrated by evaporation. After purification on silica gel (hexane/ethyl acetate 1:1), the desired product has a melting point of 165°–166° C.

Example 16
Preparation of 2-amino-thieno[2,3-d]thiazole-6-carboxylic acid methyl ester (intermediate)

Within a period of 30 minutes, 0.97 ml of bromine in 40 ml of chlorobenzene is added dropwise at −10° C., with vigorous stirring, to 4.0 g of thiomethoxycarbonyl-2-thienyl-thiourea in 50 ml of chlorobenzene. Then the mixture is stirred for one hour at approximately room temperature and is maintained at 65° C. for a further ½ hour. It is then cooled, and the precipitate is isolated by filtration, washed with a small amount of diethyl ether and triturated with 25 ml of sodium hydrogen carbonate (NaHCO$_3$; saturated solution), filtered again and washed with water. The precipitate is taken up in warm tetrahydrofuran, dried over sodium sulfate and filtered, and the filtrate is concentrated by evaporation. The residue is purified on silica gel (hexane/ethyl acetate 2:3), yielding pure product having a melting point of 221°–223° C.

TABLE 1

Compounds of the formula

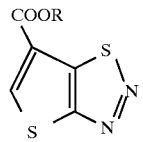

| No. | R | Physical data |
|---|---|---|
| 1.1 | H | m.p. 268–272° C.; decomp. |
| 1.2 | Na$^+$ | |
| 1.3 | NH$_4^+$ | |
| 1.4 | CH$_3$ | m.p. 140–142° C. |
| 1.5 | CH$_2$CH$_3$ | m.p. 95–97° C. |
| 1.6 | chloroethyl | |
| 1.7 | trichloroethyl | |
| 1.8 | 2-hydroxyethyl | |
| 1.9 | methoxyethyl | |
| 1.10 | 1-phenethyl | |
| 1.11 | 2-phenethyl | |
| 1.12 | n-C$_3$H$_7$ | m.p. 67–69° C. |
| 1.13 | iso-C$_3$H$_7$ | m.p. 96–98° C. |
| 1.14 | cyclopropyl | |
| 1.15 | allyl | m.p. 58–61° C. |
| 1.16 | propargyl | m.p. 103–105° C. |
| 1.17 | n-C$_4$H$_9$ | m.p. 44–45° C. |
| 1.18 | sec-C$_4$H$_9$ | m.p. 31–34° C. |
| 1.19 | tert-C$_4$H$_9$ | m.p. 90–93° C. |
| 1.20 | iso-C$_4$H$_9$ | m.p. 59–63° C. |

TABLE 1-continued

Compounds of the formula

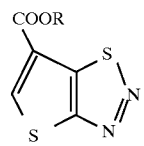

| No. | R | Physical data |
|---|---|---|
| 1.21 | cyclopropylmethyl | m.p. 79–80° C. |
| 1.22 | n-pentyl | |
| 1.23 | n-hexyl | |
| 1.24 | cyclohexyl | m.p. 69–71° C. |
| 1.25 | methyl | orange oil |
| 1.26 | (CH$_2$)$_9$CH$_3$ | m.p. 56–58° C. |
| 1.27 | CH$_2$CHC(CH$_3$)CH$_2$CH$_2$CHC(CH$_3$)$_2$ | m.p. 49–50° C. |
| 1.28 | CH$_2$COOC$_4$H$_9$ | b.p. 180–190° C./5 × 10$^{-3}$ torr |
| 1.29 | CH(CH$_3$)COOC$_2$H$_5$ | b.p. 160–170° C./10$^{-3}$ torr |
| 1.30 | phenyl | m.p. 141–143° C. |
| 1.31 | 2-chlorophenyl | |
| 1.32 | 4-methylphenyl | |
| 1.33 | 2-(methoxycarbonyl)phenyl | m.p. 151–154° C. |
| 1.34 | benzyl | m.p. 90-93° C. |
| 1.35 | 2-chlorophenyl | |
| 1.36 | 4-fluorophenyl | |
| 1.37 | 4-methylbenzyl | |
| 1.38 | 4-trifluoromethoxybenzyl | |
| 1.39 | CH$_2$-1-naphthyl | m.p. 142–145° C. |
| 1.40 | CH$_2$-2-furyl-2 | |
| 1.41 | 4-chlorophenyl | |
| 1.42 | N=cyclohexyl | |
| 1.43 | N=C(CH$_3$)C$_6$H$_5$ | |
| 1.44 | N=C(CH$_3$)COC$_6$H$_5$ | |
| 1.45 | N=C(CH$_3$)COOCH$_3$ | |

TABLE 2

Compound of the formula

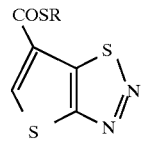

| No. | R | Physical data |
|---|---|---|
| 2.1 | CH$_3$ | m.p. 143–145° C. |
| 2.2 | CH$_2$CH$_3$ | m.p. 99–102° C. |
| 2.3 | n-C$_3$H$_7$ | m.p. 72–75° C. |
| 2.4 | iso-C$_3$H$_7$ | m.p. 80–82° C. |
| 2.5 | cyclopropyl | |
| 2.6 | C$_4$H$_9$ | |
| 2.7 | cyclopropylmethyl | |
| 2.8 | allyl | |
| 2.9 | propargyl | |
| 2.10 | CH$_2$COOCH$_3$ | m.p. 116–117° C. |
| 2.11 | CH$_2$CH$_2$COOCH$_3$ | m.p. 83–84° C. |
| 2.12 | phenyl | m.p. 150–153° C. |
| 2.13 | 2-chlorophenyl | |
| 2.14 | 4-fluorophenyl | |
| 2.15 | benzyl | m.p. 114–116° C. |
| 2.16 | 2-chlorobenzyl | |
| 2.17 | 4-methoxybenzyl | |

TABLE 3

Compounds of the formula

| No. | R₃ | R₄ | Physical data |
|---|---|---|---|
| 3.1 | H | H | m.p. 245° C.; decomp. |
| 3.2 | H | CH₃ | |
| 3.3 | H | CH₂CH₃ | m.p. 172–175° C. |
| 3.4 | H | n-Pr | |
| 3.5 | H | iso-Pr | m.p. 173–176° C. |
| 3.6 | H | n-butyl | |
| 3.7 | H | tert-butyl | m.p. 148–151° C. |
| 3.8 | | R₃R₄ piperidinyl | |
| 3.9 | | R₃R₄ morpholinyl | m.p. 114–116° C. |
| 3.10 | | R₃R₄ pyrrolidinyl | |
| 3.11 | H | CH₂COOH | |
| 3.12 | H | CH₂COCH₃ | m.p. 179–181° C. |
| 3.13 | H | CH₂COOCH₂C₆H₅ | |
| 3.14 | H | CH(CH₃)COOH | |
| 3.15 | H | CH(CH₃)COOCH₃ | m.p. 157–160° C. |
| 3.16 | H | CH(CH₃)COOCH₂C₆H₅ | |
| 3.17 | H | CH(iso-Pr)COOH | |
| 3.18 | H | CH(iso-Pr)COOCH₃ | m.p. 162–165° C. |
| 3.19 | H | CH(iso-Pr)COOCH₂C₆H₅ | |
| 3.20 | H | CH(CH₂SCH₃)COOCH₃ | m.p. 86–90° C. |
| 3.21 | H | CH(COOCH₃)CH₂CH₂COOCH₃ | amorphous |
| 3.22 | | —CH₂CH₂CH₂CHCOOCH₃ | m.p. 85–86° C. |
| 3.23 | H | phenyl | m.p. 159–160° C. |
| 3.24 | H | 2-chlorophenyl | |
| 3.25 | H | benzyl | |
| 3.26 | H | 2-fluorobenzyl | |
| 3.27 | CH₃ | CH₃ | |
| 3.28 | C₂H₅ | C₂H₅ | m.p. 102–104° C. |
| 3.29 | CH₂CH₂OH | CH₂CH₂OH | m.p. 122–124° C. |
| 3.30 | H | CH₂CH₂OH | m.p. 168–170° C. |
| 3.31 | H | cyclohexyl | |
| 3.32 | H | NHC₆H₅ | |
| 3.33 | H | NH-2-chlorophenyl | |
| 3.34 | H | NHCOOCH₂CH₃ | m.p. 183–184° C. |
| 3.35 | H | N(CH₃)₂ | m.p. 172–174° C. |
| 3.36 | H | N=C(CH₃)C₆H₅ | |
| 3.37 | H | N=cyclohexyliden-1-yl | |

TABLE 4

Compounds of the formula

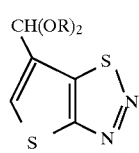

| No. | R | Physical data |
|---|---|---|
| 4.1 | CH₃ | |
| 4.2 | CH₂CH₃ | |
| 4.3 | CH₂CH₂OCH₃ | |
| 4.4 | —CH₂CH₂— | m.p. 83–86° C. |
| 4.5 | —CH(CH₃)CH₂— | |
| 4.6 | —CH(CH₂C₆H₅)CH₂— | |

TABLE 4-continued

Compounds of the formula

| No. | R | Physical data |
|---|---|---|
| 4.7 | —CH(CH₂OH)CH₂— | |
| 4.8 | —CH(CH₂OCH₃)CH₂— | |

TABLE 5

Compounds of the formula

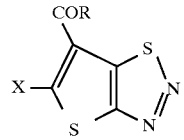

| No. | X | R | Physical data |
|---|---|---|---|
| 5.1 | H | H | m.p. 166–168° C. |
| 5.2 | H | Cl | |
| 5.3 | F | H | |
| 5.4 | F | OH | |
| 5.5 | F | OCH₃ | |
| 5.6 | F | OCH₂C₆H₅ | |
| 5.7 | F | SCH₃ | |
| 5.8 | F | SCH₂C₆H₅ | |
| 5.9 | F | NH₂ | |
| 5.10 | F | CN | |
| 5.11 | Cl | Cl | |
| 5.12 | Cl | OH | m.p. 255–256° C. |
| 5.13 | Cl | OCH₃ | m.p. 124–126° C. |
| 5.14 | Cl | OCH₂CH₃ | |
| 5.15 | Cl | SCH₃ | |
| 5.16 | Cl | SCH₂C₆H₅ | m.p. 144–146° C. |
| 5.17 | Cl | NH₂ | |
| 5.18 | Cl | NHCH(CH₃)COOCH₃ | m.p. 116–118° C. |
| 5.19 | Cl | NHCH(iso-Pr)COOCH₃ | m.p. 93–95° C. |
| 5.20 | Br | OH | |
| 5.21 | Br | OCH₃ | m.p. 156–159° C. |
| 5.22 | I | OH | m.p. 246–250° C. |
| 5.23 | I | OCH₃ | |
| 5.24 | CH₃ | OH | |
| 5.25 | CH₃ | OCH₃ | m.p. 89–91° C. |
| 5.26 | SCH₃ | OH | m.p. 295–298° C. |
| 5.27 | SCH₃ | OCH₃ | |
| 5.28 | NH₂ | OH | |
| 5.29 | NH₂ | NH₂ | |
| 5.30 | NHCOCH₃ | OH | |

TABLE 6

Compounds of the formula

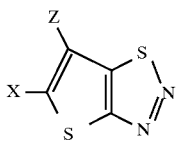

| Comp. No. | X | Z | Physical data (m.p.) |
|---|---|---|---|
| 6.1 | H | H | m.p. 78–79° C. |
| 6.2 | H | CN | m.p. 150–152° C. |
| 6.3 | H | CSOCH$_3$ | m.p. 145–148° C. |
| 6.4 | H | CSSCH(CH$_3$)$_2$ | m.p. 100–103° C. |
| 6.5 | H | CSSCH$_2$C$_6$H$_5$ | m.p. 134–137° C. |
| 6.6 | H | CSSCH$_2$CH$_2$COOCH$_3$ | m.p. 11.0–113° C. |
| 6.7 | H | CSNH$_2$ | m.p. 242–245° C. |
| 6.8 | H | CSNHCH(CH$_3$)$_2$ | m.p. 178–180° C. |
| 6.9 | H | CSNHCH(OH$_3$)COOCH$_3$ | m.p. 152–154° C. |
| 6.10 | H | CSNHCH(CH(CH$_3$)$_2$)COOCH$_3$ | m.p. 136–139° C. |
| 6.11 | H | CHNN(CH$_3$)$_2$ | m.p. 120–123° C. |
| 6.12 | H | CH$_2$OCH$_3$ | |
| 6.13 | H | CH$_2$Cl | |
| 6.14 | H | CHCl$_2$ | |
| 6.15 | H | CCl$_3$ | |
| 6.16 | H | CH$_2$Br | m.p. 242–243° C. |
| 6.17 | COOH | CH$_3$ | m.p. 79–81° C. |
| 6.18 | COOH | CH$_2$OCH$_3$ | |
| 6.19 | COOCH$_3$ | CH$_2$OCH$_3$ | m.p. 123–124° C. |
| 6.20 | COOCH$_3$ | COOCH$_3$ | m.p. 104–108° C. |
| 6.21 | COOCH$_3$ | Cl | |
| 6.22 | COOCH$_2$—C$_6$H$_5$ | CH$_3$ | |
| 6.23 | COOC$_2$H$_5$ | CH$_3$ | |
| 6.24 | CHO | CONHC(CH$_3$)$_3$ | m.p. 120–123° C. |
| 6.25 | Cl | H | m.p. 117–119° C. |
| 6.26 | Cl | H | |
| 6.27 | Cl | Cl | |
| 6.28 | Cl | CH$_3$ | |
| 6.29 | Cl | CH$_2$OCH$_3$ | |
| 6.30 | Cl | 4-methoxybenzyl | 94–97° C. |
| 6.31 | Cl | CONHN(CH$_3$)$_2$ | m.p. 158–160° C. |
| 6.32 | Cl | OCH$_2$C$_6$H$_5$ | m.p. 130–133° C. |
| 6.33 | F | CH$_3$ | |
| 6.34 | F | CH$_2$OCH$_3$ | |
| 6.35 | F | CH$_2$Cl | |
| 6.36 | Br | CH$_2$Br | |
| 6.37 | ⌈        ⌉<br>NCH₂CH₂CH₂CH₂ | COOCH$_3$ | m.p. 127–130° C. |
| 6.38 | SCH$_2$C$_6$H$_5$ | SCH$_2$C$_6$H$_5$ | m.p. 168–169° C. |
| 6.39 | H | Cl | |
| 6.40 | H | Br | |
| 6.41 | H | CH$_3$ | |

2. Formulation Examples for compounds of the Tables (throughout, percentages are by weight)

2.1 Wettable powders a) b) c)

| 2.1 Wettable powders | a) | b) | c) |
|---|---|---|---|
| a compound of the Tables | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7–8 mol of ethylene oxide) | — | 2% | — |
| highly dispersed silicic acid | 5% | 10% | 10% |
| kaolin | 62% | 27% | — |

The active ingredient is mixed with the adjuvants and the mixture is homogeneously ground in a suitable mill, affording wettable powders which can be diluted with water to give suspensions of the desired concentration.

2.2 Emulsifiable concentrate

| 2.2 Emulsifiable concentrate | |
|---|---|
| a compound of the Tables | 10% |
| octylphenol polyethylene glycol ether (4–5 mol of ethylene oxide) | 3% |
| calcium dodecylbenzenesulfonate | 3% |
| castor oil polyglycol ether (35 mol of ethylene oxide) | 4% |
| cyclohexanone | 30% |
| xylene mixture | 50% |

Emulsions of any required dilution can be obtained from this concentrate by dilution with water.

2.3 Dusts a) b)

| 2.3 Dusts | a) | b) |
|---|---|---|
| a compound of the Tables | 5% | 8% |
| talcum | 95% | — |
| kaolin | — | 92% |

Ready-for-use dusts are obtained by mixing the active ingredient with the carrier and grinding the mixture in a suitable mill.

2.4 Extruder granules

| 2.4 Extruder granules | |
|---|---|
| a compound of the Tables | 10% |
| sodium lignosulfonate | 2% |
| carboxymethylcelluose | 1% |
| kaolin | 87% |

The active ingredient is mixed and ground with the adjuvants, and the mixture is moistened with water. The mixture is extruded and then dried in a stream of air.

2.5 Coated granules

| 2.5 Coated granules | |
|---|---|
| a compound of the Tables | 3% |
| polyethylene glycol (mol. wt. 200) | 3% |
| kaolin | 94% |

(mol. wt. = molecular weight)

The finely ground active ingredient is uniformly applied, in a mixer, to the kaolin moistened with polyethylene glycol. Non-dusty coated granules are obtained in this manner.

2.6 Suspension concentrate

| 2.6 Suspension concentrate | |
|---|---|
| a compound of the Tables | 40% |
| ethylene glycol | 10% |
| nonylphenol polyethylene glycol ether (15 mol of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

3. Biological Examples

Example 3.1

Action against Colletotrichum laqenarium on Cucumis sativus L.

a) After a cultivation period of 2 weeks, cucumber plants are sprayed with a spray mixture prepared from a wettable powder formulation of the test compound (concentration: 200 ppm). After 72 hours, the plants are infected with a spore suspension ($1.0 \times 10^5$ spores/ml) of the fungus and incubated for 30 hours at high humidity and a temperature of 23° C. Incubation is then continued at normal humidity and 22° C. to 23° C. Evaluation of protective action is made 7 to 8 days after infection and is based on fungus infestation.

b) After a cultivation period of 2 weeks, cucumber plants are treated by soil application with a spray mixture prepared from a wettable powder formulation of the test compound (concentration: 20 ppm, based on the volume of the soil). After 72 hours, the plants are infected with a spore suspension ($1.5 \times 10^5$ spores/ml) of the fungus and incubated for 30 hours at high humidity and a temperature of 23° C. Incubation is then continued at normal humidity and 22° C.

Evaluation of protective action is made 7 to 8 days after infection and is based on fungus infestation.

Compounds of the Tables exhibit good activity in tests (a) and (b) and reduce fungus infestation to 0 to 20%. On the other hand, Colletotrichum infestation is 90% on untreated and infected control plants.

c) Comparison test: Direct action against Colletotrichum lagenarium

The formulated active ingredient is mixed in various concentrations (100, 10, 1, 0.1 ppm) with autoclaved and cooled nutrient medium containing 10 000 spores per ml and is poured into microtitre plates. Incubation is then carried out at 22° C. in the dark. After 2 to 3 days, fungus growth is measured by spectrophotometry.

With compounds of the Tables, no inhibit ion of fungus growth is observed; on the other hand, when the fungicide "Benomyl" (commercial product) is used as comparison substance at 0.2 ppm, 50% inhibition ($EC_{50}$) of fungus growth occurs.

Example 3.2

Action against Phytophthora infestans on tomato plants a) After a cultivation period of 3 weeks, tomato plants are sprayed with a spray mixture prepared from a wettable powder formulation of the test compound (0.02% active ingredient). After 72 hours, the treated plants are infected with a sporangia suspension of the fungus. Fungus infestation is evaluated after incubation of the infected plants for 5 days at 90–100% relative humidity and 20° C.

Compounds of the Tables exhibit good activity in the tests and reduce fungus infestation to 0 to 20%. On the other hand, Phytophthora infestation is 60% on untreated and infected control plants.

Example 3.3

Action against Pyricularia oryzae on rice plants 2-week-old rice plants are watered with a spray mixture prepared from a wettable powder formulation of the test compound (0.006% active ingredient, based on the volume of the soil). The pots are then filled with water until the lowermost parts of the stems of the rice plants are standing in water. After 96 hours, the treated rice plants are infected with a conidia suspension of the fungus Fungus infestation is evaluated after incubation of the infected plants for 5 days at 95–100% relative humidity and approximately 24° C.

In comparison with untreated control plants (100% infestation), fungus infestation on rice plants treated with a spray mixture comprising a compound of the Tables as active ingredient is only approximately 50%.

Example 3.4

Action against Cercospora nicotina on tobacco plants a) Foliar application

Tobacco plants (8 weeks old) are sprayed with a formulated solution of the test compound (concentration: 0.02% active ingredient). Four days after treatment, the plants are inoculated with a sporangia suspension of Cercospora nicotina (150 000 spores/ml), kept for 5 days in the dark at 25° C. and high humidity and then incubated further under a normal day/night sequence.

Evaluation of the symptoms in the tests is based on the leaf surface infested with fungus. Infestation is approximately 60% on the control plants; on plants treated with compounds of the Tables, infestation is 0 to 30%.

Example 3.5
Action against Erysiphe graminis on wheat

Protective action: 18-day-old wheat plants are sprayed with a formulated solution of the test compound (0.02% active ingredient). Immediately after the treatment the plants are incubated under cylinders. 24 hours later, the plants are covered. After a further 3 days, the treated plants are cut off above the primary leaf. The primary leaves are arranged horizontally and are inoculated in a dusting bell with Erysiphe graminis spores (spore density: 0.2 mg/m$^2$). The test is carried out in a climatic chamber with 12 hours of light (18 KLux), at 20° C. and 12 hours of darkness, at 18° C. Infestation is evaluated 9 and 13 days after inoculation.

Compounds of the Tables exhibit good activity in the tests and reduce fungus infestation to 0 to 20%. On the other hand, Erysiphe infestation is 70% on untreated and infected control plants.

What is claimed is:

1. A compound of formula I

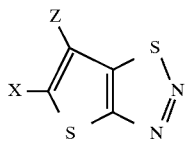

wherein:
the substituents $R_1$ are identical or different and are $C_1$–$C_4$alkyl that is unsubstituted or substituted by phenyl, $C_1$–$C_2$ alkoxy, phenoxy, or benzyloxy;

or two substituents $OR_1$ together with the carbon atom to which they are bonded, form a cyclic acetal group that is unsubstituted or substituted by $C_1$–$C_3$alkyl, phenyl, benzyl, hydroxy, or $C_1$–$C_3$hydroxyalkyl;

$R_2$ to $R_7$ are hydrogen, an unsubstituted or substituted, open-chained, saturated or unsaturated hydrocarbon radical containing up to 8 carbon atoms, an unsubstituted or substituted, cyclic, saturated or unsaturated hydrocarbon radical containing up to 10 carbon atoms, unsubstituted or substituted benzyl or phenethyl, an unsubstituted or substituted acyl group containing up to 8 carbon atoms, an unsubstituted or substituted benzoyl group, or an unsubstituted or substituted heterocyclyl radical; or $R_3$ and $R_4$, together with the nitrogen atom to which they are bonded, form a 5- or 6-membered, unsubstituted or substituted heterocycle having from 1 to 3 hetero atoms selected from O, S, and N; or $R_6$ and $R_7$, together with the atom to which they are bonded, form a 5- to 7-membered unsubstituted or substituted carbocyclic or heterocyclic ring having from 1 to 3 hetero atoms selected from O, S, and N;

$R_8$, $R_9$, and $R_{10}$ is each hydrogen, $C_1$–$C_4$alkyl, benzyl, $C_1$–$C_4$acyl, or benzoyl;

A is hydrogen, halogen, $OR_2$, $SR_2$, $N(R_3)R_4$, NH—$OR_5$, O—$NCR_6R_7$, O—N $R_6R_7$, NH—$NCR_6R_7$, or NH—$NR_6R_7$;

X is hydrogen, halogen, $C_1$–$C_4$alkyl, $SR_8$, $N(R_9)R_{10}$, $CH_2OH$, CHO, or $COOR_8$; and Z is hydrogen, halogen, unsubstituted methyl, CN, CO—A, CS—A, or $CH(OR_1)_2$; in free form or in the form of a salt;

with the proviso that when Z is methyl, X is not $COOC_2H_5$.

2. A compound of claim 1, wherein:
$R_1$ is $C_1$–$C_4$alkyl;

or two substituents $OR_1$, together with the carbon atom to which they are bonded, form a 5- to 7-membered cyclic acetal group that is unsubstituted or substituted by $C_1$–$C_3$ alkyl;

$R_2$ and $R_3$ are hydrogen; $C_1$–$C_8$alkyl that is unsubstituted or substituted by from 1 to 5 halogen atoms, $C_3$–$C_6$cycloalkyl, $C_1$–$C_4$alkoxy, phenoxy, benzyloxy, $C_1$–$C_4$acyloxy, benzoyloxy, hydroxy, nitro, cyano, $C_1$–$C_4$alkanoyl, benzoyl, carboxy, $C_1$–$C_4$alkoxycarbonyl, benzyloxycarbonyl, amino, $C_1$–$C_4$alkylamino, $C_1$–$C_4$dialkylamino, or heterocyclyl;

$C_3$–$C_6$alkenyl that is unsubstituted or substituted by from 1 to 5 halogen atoms;

$C_3$–$C_6$alkynyl; $C_3$–$C_6$cycloalkyl; $C_1$–$C_4$alkanoyl; phenyl, benzyl or phenethyl, the phenyl rings of which are unsubstituted or mono- to tri-substituted by halogen, hydroxy, $C_1$–$C_4$alkyl, halo-$C_1$–$C_2$alkyl, $C_1$–$C_2$alkoxy, halo-$C_1$–$C_2$alkoxy, or nitro; or naphthyl, benzoyl, or heterocyclyl, each of which is unsubstituted or mono- to tri-substituted by identical or different substituents selected from halogen, $C_1$–$C_2$alkyl, halomethyl, and nitro;

$R_4$ is hydrogen, $C_1$–$C_6$alkyl, or benzyl; or $R_3$ and $R_4$, together with the nitrogen atom to which they are bonded, form a 5- or 6-membered ring having 1 or 2 hetero atoms selected from O, S, and N, said ring being unsubstituted or mono- or di-substituted by identical or different substituents selected from halogen, $C_1$–$C_3$alkyl, and $C_1$–$C_2$alkoxycarbonyl;

$R_5$, $R_6$, and $R_7$ is each independently hydrogen, $C_1$–$C_6$alkyl, $C_3$–$C_4$alkenyl, $C_3$–$C_4$alkynyl, $C_3$–$C_6$cycloalkyl, or phenyl or benzyl, the phenyl rings of which are unsubstituted or mono- or di-substituted by halogen, hydroxy, $C_1$–$C_2$alkyl, $C_1$–$C_2$alkoxy, halomethyl, or halomethoxy;

or $R_6$ and $R_7$, together with the atom to which they are bonded, form a 5- to 7-membered carbocyclic or heterocyclic ring having from 1 to 3 hetero atom selected from O, S, and N, said ring being unsubstituted or mono- to tri-substituted by identical or different substituents selected from halogen and $C_1$–$C_3$alkyl.

3. A compound of claim 1, wherein Z is COA, CS—A, or $CH(OR_1)_2$.

4. A compound of claim 1, wherein:
Z is CO—A;

A is hydrogen, $OR_2$, $SR_2$, $N(R_3)R_4$, NH—O $R_5$, O—$NCR_6R_7$, O—N $R_6R_7$, NH—$NCR_6R_7$; or NH—$NR_6R_7$;

$R_2$ and $R_3$ are hydrogen; $C_1$–$C_8$alkyl that is unsubstituted or substituted by from 1 to 5 halogen atoms, $C_3$–$C_6$cycloalkyl, $C_1$–$C_4$alkoxy, phenoxy, benzyloxy, $C_1$–$C_4$acyloxy, benzoyloxy, hydroxy, nitro, cyano, $C_1$–$C_4$alkanoyl, benzoyl, carboxy, $C_1$–$C_4$alkoxycarbonyl, benzyloxycarbonyl, amino, $C_1$–$C_4$alkylamino, $C_1$–$C_4$dialkylamino, or heterocyclyl; $C_3$–$C_6$alkenyl that is unsubstituted or substituted by from 1 to 5 halogen atoms; $C_3$–$C_6$alkynyl; $C_3$–$C_6$cycloalkyl; $C_1$–$C_4$alkanoyl; phenyl, benzyl, or phenethyl, the phenyl rings of which are unsubstituted or mono- to tri-substituted by halogen, hydroxy, $C_1$-$C_4$alkyl, halo-$C_1$-$C_2$alkyl, $C_1$-$C_2$alkoxy, halo-$C_1$-$C_2$alkoxy, or nitro; or naphthyl, benzoyl, or heterocyclyl, each of which is unsubstituted or mono- to tri-substituted by identical or different substituents selected from halogen, $C_1$-$C_2$alkyl, halomethyl, and nitro; or $R_3$ and $R_4$, together with the nitrogen atom to which they are bonded, form a 5- or 6-membered ring having 1 or 2 hetero atom selected from O, S, and N, said ring being unsubstituted or mono- or di-substituted by identical or different substituents selected from halogen and $C_1$-$C_3$alkyl;

$R_5$, $R_6$ and $R_7$ is each independently hydrogen, $C_1$-$C_6$alkyl, $C_3$-$C_4$alkenyl, $C_3$-$C_4$alkynyl, $C_3$-$C_6$cycloalkyl, or phenyl or benzyl, the phenyl rings of which are unsubstituted or mono- or di-substituted by halogen, hydroxy, $C_1$-$C_2$alkyl, $C_1$-$C_2$alkoxy, halomethyl, or halomethoxy;

or $R_6$ and $R_7$, together with the atom to which they are bonded, form a 5- to 7-membered carbocyclic or heterocyclic ring having from 1 to 3 hetero atoms selected from O, S, and N, said ring being unsubstituted or mono- to tri-substituted by identical or different substituents selected from halogen, $C_1$-$C_3$alkyl, and $C_1$-$C_2$alkoxycarbonyl.

5. A compound of claim 4, wherein Z is CO—A and A is $OR_2$ or $SR_2$.

6. A compound of claim 5, wherein:

$R_2$ is hydrogen; $C_1$-$C_6$alkyl that is unsubstituted or substituted by from 1 to 3 halogen atoms, $C_3$-$C_6$cycloalkyl, $C_1$-$C_2$alkoxy, phenoxy, hydroxy, cyano, $C_1$-$C_2$alkanoyl, benzoyl, carboxy, $C_1$-$C_4$alkoxycarbonyl, benzyloxycarbonyl, $C_1$-$C_2$acyloxy, benzoyloxy, amino, $C_1$-$C_4$alkylamino, or $C_1$-$C_4$dialkylamino; $C_3$-$C_4$alkenyl that is unsubstituted or substituted by from 1 to 3 halogen atoms; $C_3$-$C_4$alkynyl; $C_3$-$C_6$cycloalkyl; or phenyl, benzyl, or phenethyl, the phenyl rings of which are unsubstituted or mono- or di-substituted by halogen, hydroxy, $C_1$-$C_4$alkyl, halo-$C_1$-$C_2$alkyl, $C_1$-$C_2$alkoxy, halo-$C_1$-$C_2$alkoxy, or nitro.

7. A compound of claim 1, wherein Z is CO—$OR_2$.

8. A compound of claim 1, wherein:

Z is CN or CO—$N(R_3)R_4$;

$R_3$ is hydrogen; $C_1$-$C_5$alkyl that is unsubstituted or substituted by from 1 to 3 halogen atoms, $C_3$-$C_6$cycloalkyl, $C_1$-$C_2$alkoxy, phenoxy, hydroxy, cyano, $C_1$-$C_2$alkanoyl, benzoyl, carboxy, $C_1$-$C_4$alkoxycarbonyl, benzyloxycarbonyl, $C_1$-$C_2$acyloxy, benzoyloxy, amino, $C_1$-$C_4$alkylamino, or $C_1$-$C_4$dialkylamino; $C_3$-$C_4$alkenyl that is unsubstituted or substituted by from 1 to 3 halogen atoms; $C_3$-$C_4$alkynyl; $C_3$-$C_6$cycloalkyl; or phenyl, benzyl, or phenethyl, the phenyl rings of which are unsubstituted or mono- or di-substituted by halogen, hydroxy, $C_1$-$C_4$alkyl, halo-$C_1$-$C_2$alkyl, $C_1$-$C_2$alkoxy, halo-$C_1$-$C_2$alkoxy, or nitro;

$R_4$ is hydrogen, $C_1$-$C_6$alkyl, or benzyl; or $R_3$ and $R_4$, together with the nitrogen atom to which they are bonded, are pyrrolidinyl, piperidinyl, morpholinyl, or dimethylmorpholinyl.

9. A compound of claim 1, wherein

Z is CHO or $CH(OR_1)_2$;

the substituents $R_1$ are identical or different and are $C_1$-$C_1$alkyl that is unsubstituted or substituted by phenyl, $C_1$-$C_2$alkoxy, phenoxy, or benzyloxy; or two substituents $OR_1$, together with the carbon atom to which they are bonded, form a 5- or 6-membered cyclic acetal group that is unsubstituted or substituted by $C_1$-$C_3$alkyl, phenyl, benzyl, hydroxy, or $C_1$-$C_3$hydroxyalkyl.

10. A compound of claim 1, wherein Z is hydrogen, methyl, halogen, $C_1$-$C_4$alkoxymethyl, or halomethyl.

11. A compound of claim 1, wherein X is hydrogen, halogen, methyl, mercapto, methylthio, or amino.

12. A compound of claim 1, wherein X is hydrogen.

13. A solution in an aprotic solvent of an organolithium compound of formula III

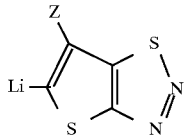

wherein:

A is hydrogen, halogen, $OR_2$, $SR_2$, $N(R_3)R_4$, NH—$OR_5$, O—$NCR_6R_7$, O—N $R_6R_7$, NH—$NCR_6R_7$, or NH—$NR_6R_7$;

Z is hydrogen, halogen, unsubstituted methyl, CN, CO—A, CS—A, or $CH(OR_1)_2$;

the substituents $R_1$ are identical or different and are $C_1$-$C_4$alkyl that is unsubstituted or substituted by phenyl, $C_1$-$C_2$ alkoxy, phenoxy, or benzyloxy;

or two substituents $OR_1$ together with the carbon atom to which they are bonded, form a cyclic acetal group that is unsubstituted or substituted by $C_1$-$C_3$alkyl, phenyl, benzyl, hydroxy, or $C_1$-$C_3$hydroxyalkyl;

$R_2$ to $R_7$ are hydrogen, an unsubstituted or substituted, open-chained, saturated or unsaturated hydrocarbon radical containing up to 8 carbon atoms, an unsubstituted or substituted, cyclic, saturated or unsaturated hydrocarbon radical containing up to 10 carbon atoms, unsubstituted or substituted benzyl or phenethyl, an unsubstituted or substituted acyl group containing up to 8 carbon atoms, an unsubstituted or substituted benzoyl group, or an unsubstituted or substituted heterocyclyl radical; or $R_3$ and $R_4$, together with the nitrogen atom to which they are bonded, form a 5- or 6-membered, unsubstituted or substituted heterocycle having from 1 to 3 hetero atoms selected from O, S, and N; or $R_6$ and $R_7$, together with the atom to which they are bonded, form a 5- to 7-membered, unsubstituted or substituted carbocyclic or heterocyclic ring having from 1 to 3 hetero atoms selected from O, S, and N.

14. A composition comprising, in an amount effective for protecting plants against attack by microorganisms, 1) a compound of claim 1, in free form or in the form of an agrochemically acceptable salt, and 2) a carrier therefor.

15. A method of protecting plants against attack by microorganisms which comprises applying an amount, effective for protecting plants against attack by said microorganisms, of a compound of claim 1 to the plants, to parts of the plants, and/or to the locus of the plants.

16. A method of immunizing plants against attack by microorganisms which comprises applying an amount, effective for protecting plants against attack by said microorganisms, amount of a compound of claim 1 to the plants, to parts of the plants, and/or to the locus of the plants.

* * * * *